US007507843B2

(12) United States Patent
Song et al.

(10) Patent No.: US 7,507,843 B2
(45) Date of Patent: Mar. 24, 2009

(54) STEREOSELECTIVE SYNTHESIS OF CERTAIN TRIFLUOROMETHYL-SUBSTITUTED ALCOHOLS

(75) Inventors: Jinhua J. Song, Hopewell Junction, NY (US); Zhulin Tan, Danbury, CT (US); Jinghua Xu, Bethel, CT (US); Nathan K. Yee, Danbury, CT (US); Chris H. Senanayake, Brookfield, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 440 days.

(21) Appl. No.: 10/955,165

(22) Filed: Sep. 30, 2004

(65) Prior Publication Data

US 2005/0131241 A1 Jun. 16, 2005

Related U.S. Application Data

(60) Provisional application No. 60/511,744, filed on Oct. 16, 2003.

(51) Int. Cl.
*C07D 301/27* (2006.01)
(52) U.S. Cl. .................................... 549/514
(58) Field of Classification Search ................. 549/516, 549/514
See application file for complete search history.

(56) References Cited

U.S. PATENT DOCUMENTS

| | | | |
|---|---|---|---|
| 4,880,839 A | 11/1989 | Tucker | |
| 5,039,691 A | 8/1991 | Spagnuolo et al. | |
| 6,187,918 B1 * | 2/2001 | Nugent | 544/170 |
| 6,323,199 B1 | 11/2001 | Lehmann et al. | |
| 6,329,534 B1 | 12/2001 | Kym et al. | |
| 6,362,344 B1 * | 3/2002 | Nugent | 549/79 |
| 6,380,223 B1 | 4/2002 | Dow et al. | |
| 6,436,986 B1 | 8/2002 | Kym et al. | |
| 6,506,766 B1 | 1/2003 | Coghlan et al. | |
| 6,583,180 B2 | 6/2003 | Link et al. | |
| 2002/0077356 A1 | 6/2002 | Jaroch et al. | |
| 2002/0156311 A1 | 10/2002 | Link et al. | |
| 2003/0232823 A1 | 12/2003 | Betageri et al. | |
| 2004/0010020 A1 | 1/2004 | Kirrane, Jr. et al. | |
| 2004/0010148 A1 | 1/2004 | Kirrane, Jr. et al. | |
| 2004/0029932 A1 | 2/2004 | Bekkali et al. | |
| 2004/0097574 A1 | 5/2004 | Marshall | |
| 2004/0116455 A1 | 6/2004 | Bekkali et al. | |
| 2004/0116694 A1 | 6/2004 | Jaroch et al. | |
| 2004/0162321 A1 | 8/2004 | Kuzmich et al. | |
| 2004/0224992 A1 | 11/2004 | Cywin et al. | |

FOREIGN PATENT DOCUMENTS

| | | |
|---|---|---|
| BE | 900594 | 9/1984 |
| EP | 0 154 528 A2 | 3/1985 |
| EP | 0 154 528 A3 | 3/1985 |
| EP | 0 253 500 | 2/1991 |
| EP | 0 253 503 | 12/1991 |
| GB | 2 146 987 A | 9/1984 |
| WO | WO 96/19458 | 6/1996 |
| WO | WO 97/27852 | 8/1997 |
| WO | WO 98/54159 | 12/1998 |
| WO | WO 99/41256 | 2/1999 |
| WO | WO 00/32584 | 6/2000 |
| WO | WO 00/66522 | 11/2000 |
| WO | WO 02/02565 | 1/2002 |
| WO | WO 02/10143 | 2/2002 |
| WO | WO 02/064550 | 8/2002 |
| WO | WO 03/059899 A1 | 7/2003 |
| WO | WO 03/082827 A1 * | 9/2003 |
| WO | WO 03/082827 A1 | 10/2003 |

OTHER PUBLICATIONS

Song et al. Journal of Organic Chemistry, 2007, 72, 292-294.*
Hamann, Lawrence, et al ; Discovery of a potent, Orally active Nonsteroidal Androgen Receptor Agonist: 4-Ethyl-1,2,3,4-tetrahydro-6-(trifluoromethyl)-8-pyridono[5,6-g]quinoline(LG121071), J. Med Chem 1999, 42, 210-212.

(Continued)

*Primary Examiner*—D. Margaret Seaman
*Assistant Examiner*—Nizal S Chandrakumar
(74) *Attorney, Agent, or Firm*—Michael P. Morris; Mary-Ellen M. Devlin; Timothy X. Witkowski

(57) ABSTRACT

A process for stereoselective synthesis of compounds of Formula X

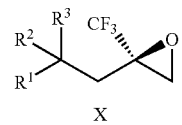

wherein:
$R^1$ is an aryl or heteroaryl group, each optionally independently substituted with one to three substituent groups, wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, $C_1$-$C_5$ alkanoyloxy, $C_1$-$C_5$ alkanoyl, aroyl, trifluoromethyl, trifluoromethoxy, or $C_1$-$C_5$ alkylthio,
wherein each substituent group of $R^1$ is optionally independently substituted with one to three substituent groups selected from methyl, methoxy, fluoro, chloro, hydroxy, oxo, cyano, or amino; and
$R^2$ and $R^3$ are each independently hydrogen or $C_1$-$C_5$ alkyl, or $R^2$ and $R^3$ together with the carbon atom they are commonly attached to form a $C_3$-$C_8$ spiro cycloalkyl ring.

27 Claims, No Drawings

OTHER PUBLICATIONS

Pooley, Charlotte, et al; Discovery and Preliminary SAR Studies of a Novel Nonsteroidal Progesterone Receptor Antagonist Pharmacophore, J. Med. Chem 1998, 41, 3461-3466.

Edwards, James, P. et al; 5-Aryl-1,2-dihydro-5H-chromeno[3,4-f]quinolines as Potent, Orally Active, Nonsteroidal Progestgerone Receptor Agonists; The Effect of D-Ring Substituents, J. Med. Chem 1998, 41, 303-310.

Zhi, Lin, et al; 5-Aryl-1,2-dihydro-5H-chromeno[3,4-f]quinolines: A Novel Class of Nonsteroidal Human Progesterone Receptor Agonists, J. Med. Chem 1998, 41, 291-302.

Zhi, Lin; et al 5-Aryl-1,2,3,4-tetrahydrochromeno[3,4-f]quinolin-3-ones as a Novel Class Of Nonsteroidal Progesterone Receptor Agonists: Effect of A-Ring Modification, J. Med. Chem 1999, 42, 1466-1472.

Tegley, Christopher, et al; 5-Benzylidene 1,2-Dihydrochromeno[3,4-f]quinolines, A Novel Class of Nonsteroidal Human Progesterone Receptor Agonists; J. Med. Chem 1998, 41, 4354-4359.

Edwards, James, P. et al; Preparation, Resolution and Biological Evaluation of 5-Aryl-1,2-dihydro-5H-chromeno[3,4-f]quinolines as Potent, Orally Active, Nonsteroidal Progestgerone Receptor Agonists: J. Med. Chem. 1998, 41, 2779-2785.

Hamann, Lawrence, et al; Synthesis and Biological Activity of a Novel Series of Nonsteroidal, Peripherally Selective androgen Receptor Antagonists Derived from 1,2-Dihydropyridono[5,6-g] quinolines J. Med. Chem 1998, 41, 623-639.

English Translation of WO/02/10143.

Iseki, K. et al; "Asymmetric Trifluoromethylation of Aldehydes and Ketones with Trifluoromethyltrimethylsilane Catalysed by Chiral Quarternary Ammonium Fluorides"; Tetrahedron Letters, vol. 35, No. 19, 1994, pp. 3137-3138, XP 002313212.

Prakash, et al; "Asymmetric Synthesis of Trifluoromethylated Allylic Amines Using alpha,beta-Unsaturated N-tert-Butanesulfinimines", Organic Letters, 2001, vol. 3, No. 18, pp. 2847-2850.

Ramaiah, et al; "Direct Trifluoromethylation of alpha-Keto Esters to beta,beta,beta-Trifluorolactic Acid Derivatives Using Trifluoromethyltrimethylsilane"; Synlett, 1991, vol. 9, pp. 643-644.

Hagiwara, et al; Main Group Chem. 1997, vol. 2, p. 13.

* cited by examiner

US 7,507,843 B2

STEREOSELECTIVE SYNTHESIS OF CERTAIN TRIFLUOROMETHYL-SUBSTITUTED ALCOHOLS

RELATED APPLICATIONS

This application claims benefit of U.S. Ser. No. 60/511,744, filed Oct. 16, 2003, which is hereby incorporated by reference in its entirety.

FIELD OF THE INVENTION

The present invention relates to the stereoselective synthesis of certain trifluoromethyl-substituted alcohols.

BACKGROUND OF THE INVENTION

Trifluoromethyl-substituted alcohols of formula (I) have been described as ligands that bind to the glucocorticoid receptor. These compounds are effective as therapeutics in treating a number of diseases modulated by glucocorticoid receptor function, including inflammatory, autoimmune and allergic disorders. Examples of these compounds are described in U.S. patent application Pub. Nos. 2003/0232823 (corresponding to PCT International Publication No. WO 03/059899), 2004/0029932 (corresponding to PCT International Publication No. WO 03/082787), and 2004/0023999 (corresponding to PCT International Publication No. WO 03/082280), which are each incorporated herein by reference in their entireties and are hereinafter termed "the Trifluoromethyl-Substituted Alcohol Patent Applications".

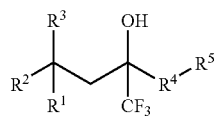

(I)

It is well known in the art that enantiomers of a particular compound can have different biological properties including efficacy, toxicity, and pharmacokinetic properties. Thus, it is often desirable to administer one enantiomer of a racemic therapeutic compound.

The synthetic methods disclosed in the patent applications cited above describe the synthesis of racemic products. Separation of enantiomers was accomplished by chiral HPLC and may be accomplished by other conventional ways of separating enantiomers. Chiral HPLC and other enantiomer separation method, however, are generally unsuitable for large-scale preparation of a single enantiomer. Thus, a stereoselective synthesis for preparation of these compounds would be highly desirable.

The present invention discloses a stereoselective synthesis of certain compounds of formula (I). The key step involves a novel, chiral auxiliary controlled addition of trifluoromethide ion, generated from trifluoromethyltrimethylsilane (TMS-$CF_3$) and fluoride ion, to a keto-ester. There are no examples of chiral auxiliary controlled $CF_3$ addition to carbonyl groups in the chemical literature. One report describes the stereoselective addition of trifluoromethide ion to α,β-unsaturated N-tert-butanesulfinimines to prepare trifluoromethylated allylic amines (G. K. Surya Prakash et al., *Org. Lett.*, 2001, 3, 2847).

P. Ramaiah and G. K. Surya Prakash (*Synlett*, 1991, 9, 643) describe the preparation of racemic 2-hydroxy-2-(trifluoromethyl)alkanoic esters by addition of trifluoromethide ion generated from TMS-$CF_3$ and fluoride ion to α-ketoesters. K. Iseki et al. (*Tetrahedron Lett.*, 1994, 35, 3137) describe the asymmetric trifluoromethylation of aldehydes and ketones with TMS-$CF_3$ in the presence of catalytic chiral quaternary ammonium fluorides. Enantiomeric excesses between 15% and 51% were reported. This method was found to be unsuitable for our substrate, proceeding very sluggishly and giving less than 1% conversion. T. Hagiwara et al. (*Main Group Chem*, 1997, 2, 13) demonstrated addition of $CF_3$ to aldehydes in 9% enantiomeric excess by reaction with TMS-$CF_3$ in the presence of a chiral Lewis base catalyst (quinine). No reaction was observed, however, when this system was applied to our substrate of interest.

SUMMARY OF THE INVENTION

The instant invention is directed to a process for stereoselective synthesis of a compound of Formula X

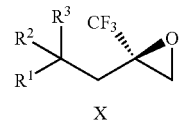

X wherein:

$R^1$ is an aryl or heteroaryl group, each optionally independently substituted with one to three substituent groups,
  wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, $C_1$-$C_5$ alkanoyloxy, $C_1$-$C_5$ alkanoyl, aroyl, trifluoromethyl, trifluoromethoxy, or $C_1$-$C_5$ alkylthio,
    wherein each substituent group of $R^1$ is optionally independently substituted with one to three substituent groups selected from methyl, methoxy, fluoro, chloro, or hydroxy; and $R^2$ and $R^3$ are each independently hydrogen or $C_1$-$C_5$ alkyl, or $R^2$ and $R^3$ together with the carbon atom they are commonly attached to form a $C_3$-$C_8$ spiro cycloalkyl ring;

the process comprising:

(a) reacting the starting material of formula A where X is Cl, Br, or I, with magnesium metal in a suitable solvent to prepare a Grignard intermediate of formula B

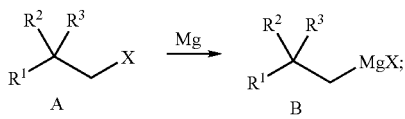

(b) reacting the Grignard intermediate of formula B with a disubstituted oxalate of formula C, where $R^{10}$ is an alkyl or aryl group, in a suitable solvent to obtain a compound of formula D

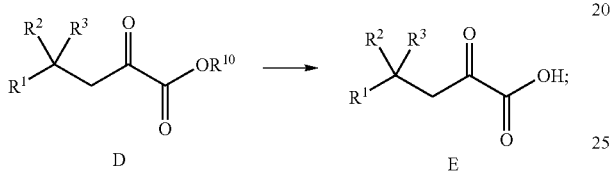

B + C →

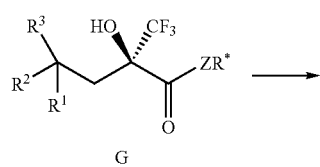

D (c) hydrolyzing the compound of formula D in a suitable solvent to obtain the carboxylic acid of formula E

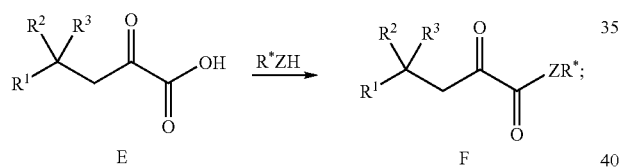

D → E (d) coupling the carboxylic acid of formula E with R*ZH, where R*ZH is a chiral auxiliary and R* is a chiral residue and Z is O or NH, in a suitable solvent to obtain a compound of formula F

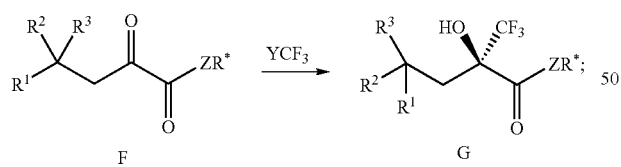

E → F (e) reacting the compound of formula F with trifluoromethide ion source $YCF_3$ in a suitable solvent to make the compound of formula G

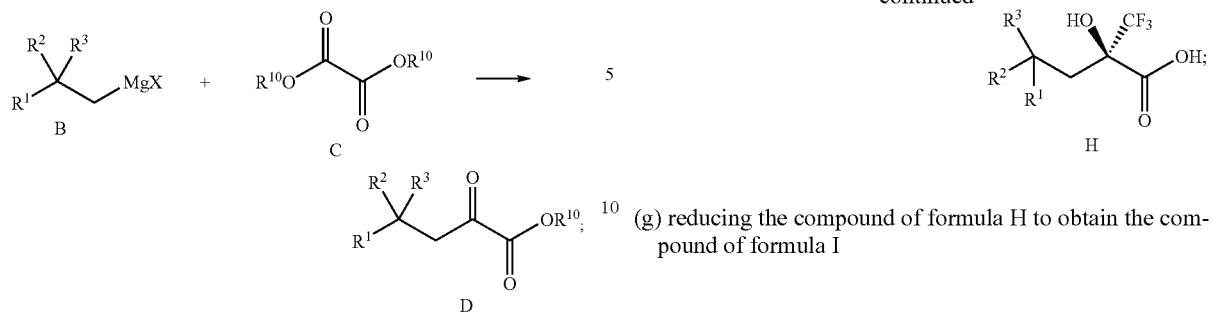

F → G (f) hydrolyzing the compound of formula G to remove the chiral auxiliary group R*ZH and obtain the compound of formula H

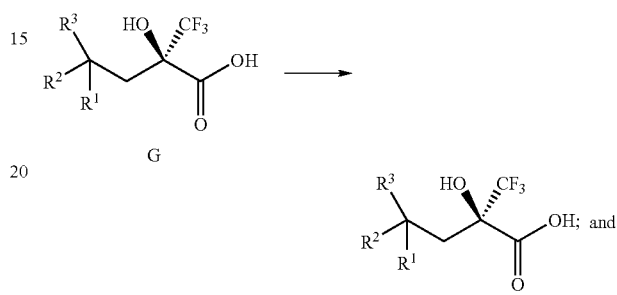

G → H (g) reducing the compound of formula H to obtain the compound of formula I

H → G → I (h) cyclizing the compound of formula I to obtain the epoxide compound of formula X

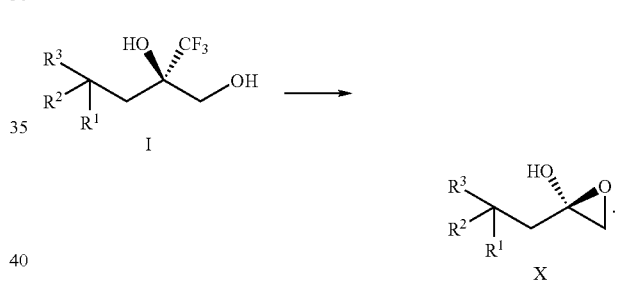

I → X

In an aspect of the invention, the suitable solvent of step (a) is selected from dimethyl ether, diethyl ether, dipropyl ether, diisopropyl ether, dibutyl ether, tetrahydrofuran (THF), ethylene glycol dimethyl ether (DME), tert-butyl methyl ether (MTBE), or a mixture thereof, preferably diethyl ether or tetrahydrofuran.

In another aspect of the invention, the suitable solvent of step (b) is selected from diethyl ether, dipropyl ether, diisopropyl ether, dibutyl ether, tetrahydrofuran (THF), ethylene glycol dimethyl ether (DME), tert-butyl methyl ether (MTBE), or a mixture thereof, preferably diethyl ether or tetrahydrofuran.

In yet another aspect of the invention, the hydrolysis of step (c) is accomplished with an alkaline metal hydroxide, phase transfer hydrolysis, or acid hydrolysis in a suitable solvent selected from tetrahydrofuran (THF), methanol, ethanol, water, DME, MTBE, IPA, dimethyl ether, dipropyl ether, diisopropyl ether, or mixture of these solvents, preferably dimethyl ether, diethyl ether, tetrahydrofuran (THF), or a mixture thereof.

In another aspect of the invention, the suitable solvent of step (d) is selected from: toluene, benzene, xylene, hexane, pentane, heptane, acetonitrile, methylene chloride, ethyl acetate, or a mixture thereof.

In still another aspect of the invention, the reaction of step (d) is accomplished using a condensing agent, preferably 1,3-dicyclohexylcarbodiimide (DCC) or 1-(dimethylaminopropy)-3-ethylcarbodiimide hydrochloride (EDC), or a Larock condensing agent as defined herein.

In still another aspect of the invention, R*ZH is a Seyden-Penne chiral auxiliary as defined herein or is menthol, 8-phenylmenthol, trans-2-phenyl-1-cyclohexanol, a norephedrine-derived chiral alcohol, or a cis-aminoindinol-derived chiral alcohol.

In another aspect of the invention, the suitable solvent of step (e) is selected from: diethyl ether, methylene chloride, toluene, benzene, acetonitrile, N,N-dimethylformamide (DMF), tetrahydrofuran (THF), tert-butyl methyl ether (MTBE), or a mixture thereof.

In still another aspect of the invention, the chiral auxiliary group R*ZH is recovered in the form of a compound during or after step (f).

In another aspect of the invention, the trifluoromethide ion source $YCF_3$ is selected from $TMS-CF_3$ and $TES-CF_3$.

In another aspect of the invention, an initiator is used in step (e), preferably tetrabutylammonium fluoride (TBAF), tetrabutylammonium triphenyldifluorosilicate (TBAT), a trialkylamine, a trialkylphosphine, cesium fluoride, potassium fluoride, DMAP, or pyridine.

In yet another aspect of the invention, the hydrolysis of step (f) is accomplished using a hydrolyzing agent, preferably KOH/ROH, where R is a lower alkyl group.

In still another aspect of the invention, the reduction of step (g) is accomplished using a reducing agent selected from diisobutylaluminum hydride (DIBAL), 65 wt. % solution of sodium bis(2-methoxyethoxy)aluminum hydride in toluene (Red-Al®), borane-iodine complex, borane-sulfuric acid complex, lithium aluminum hydride (LAH), or 9-borabicyclo [3.3.1]nonane (9-BBN).

In another aspect of the invention, the suitable solvent of step (g) is selected from diethyl ether, toluene, tetrahydrofuran (THF), tert-butyl methyl ether (MTBE), hexanes, or a mixture thereof.

In still another aspect of the invention, the cyclizing of step (h) is accomplished using a sulfonyl halide, preferably mesitylenesulfonyl chloride (MsCl) or p-toluenesulfonyl chloride (TsCl).

In yet another aspect of the invention, the cyclizing of step (h) is accomplished with a suitable organic or inorganic base, preferably triethylamine (TEA), diisopropylethylamine (DIEA), pyridine, lutidine, or potassium carbonate.

It should also be noted that the invention should be understood to include none, some, or all of these various aspects in various combination.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $C_1$-$C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar-, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl(isopropyl), n-butyl, n-pentyl, 1,1-dimethylethyl (tert-butyl), and the like. It may be abbreviated "Alk".

The terms "alkenyl" or "alkenyl group" mean a branched or straight-chain aliphatic hydrocarbon monovalent radical containing at least one carbon-carbon double bond. This term is exemplified by groups such as ethenyl, propenyl, n-butenyl, isobutenyl, 3-methylbut-2-enyl, n-pentenyl, heptenyl, octenyl, decenyl, and the like.

The terms "alkynyl" or "alkynyl group" mean a branched or straight-chain aliphatic hydrocarbon monovalent radical containing at least one carbon-carbon triple bond. This term is exemplified by groups such as ethynyl, propynyl, n-butynyl, 2-butynyl, 3-methylbutynyl, n-pentynyl, heptynyl, octynl, decynl, and the like.

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkenylene" or "alkenylene group" mean a branched or straight-chain aliphatic hydrocarbon divalent radical having the specified number of carbon atoms and at least one carbon-carbon double bond. This term is exemplified by groups such as ethenylene, propenylene, n-butenylene, and the like, and may alternatively and equivalently be denoted herein as -(alkylenyl)-.

The terms "alkynylene" or "alkynylene group" mean a branched or straight-chain aliphatic hydrocarbon divalent radical containing at least one carbon-carbon triple bond. This term is exemplified by groups such as ethynylene, propynylene, n-butynylene, 2-butynylene, 3-methylbutynylene, n-pentynylene, heptynylene, octynylene, decynylene, and the like, and may alternatively and equivalently be denoted herein as -(alkynyl)-.

The terms "alkoxy" or "alkoxy group" mean a monovalent radical of the formula AlkO—, where Alk is an alkyl group. This term is exemplified by groups such as methoxy, ethoxy, propoxy, isopropoxy, butoxy, sec-butoxy, tert-butoxy, pentoxy, and the like.

The terms "aryloxy", "aryloxy group", mean a monovalent radical of the formula ArO—, where Ar is aryl. This term is exemplified by groups such as phenoxy, naphthoxy, and the like.

The terms "alkylcarbonyl", "alkylcarbonyl group", "alkanoyl", or "alkanoyl group" mean a monovalent radical of the formula AlkC(O)—, where Alk is alkyl or hydrogen.

The terms "arylcarbonyl", "arylcarbonyl group", "aroyl" or "aroyl group" mean a monovalent radical of the formula ArC(O)—, where Ar is aryl.

The terms "acyl" or "acyl group" mean a monovalent radical of the formula RC(O)—, where R is a substituent selected from hydrogen or an organic substituent. Exemplary substituents include alkyl, aryl, arylalkyl, cycloalkyl, heterocyclyl, heteroaryl, heteroarylalkyl, and the like. As such, the terms comprise alkylcarbonyl groups and arylcarbonyl groups.

The terms "acylamino" or "acylamino group" mean a monovalent radical of the formula RC(O)N(R)—, where each R is a substituent selected from hydrogen or a substituent group.

The terms "alkoxycarbonyl" or "alkoxycarbonyl group" mean a monovalent radical of the formula AlkO-C(O)—, where Alk is alkyl. Exemplary alkoxycarbonyl groups include methoxycarbonyl, ethoxycarbonyl, tert-butyloxycarbonyl, and the like.

The terms "alkylaminocarbonyloxy" or "alkylaminocarbonyloxy group" mean a monovalent radical of the formula $R_2NC(O)O$—, where each R is independently hydrogen or lower alkyl.

The term "alkoxycarbonylamino" or "alkoxycarbonylamino group" mean a monovalent radical of the formula ROC(O)NH—, where R is lower alkyl.

The terms "alkylcarbonylamino" or "alkylcarbonylamino group" or "alkanoylamino" or "alkanoylamino groups" mean a monovalent radical of the formula AlkC(O)NH—, where Alk is alkyl. Exemplary alkylcarbonylamino groups include acetamido ($CH_3C(O)NH$—).

The terms "alkylaminocarbonyloxy" or "alkylaminocarbonyloxy group" mean a monovalent radical of the formula AlkNHC(O)O—, where Alk is alkyl.

The terms "amino" or "amino group" mean an —$NH_2$ group.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula —$NR_2$, where each R is independently a substituent selected from hydrogen or the specified substituents (but where both Rs cannot be hydrogen). Exemplary substituents include alkyl, alkanoyl, aryl, arylalkyl, cycloalkyl, heterocyclyl, heteroaryl, heteroarylalkyl, and the like.

The terms "alkoxycarbonylamino" or "alkoxycarbonylamino group" mean a monovalent radical of the formula AlkOC(O)NH—, where Alk is alkyl.

The terms "ureido" or "ureido group" mean a monovalent radical of the formula $R_2NC(O)NH$—, where each R is independently hydrogen or alkyl.

The terms "halogen" or "halogen group" mean a fluoro, chloro, bromo, or iodo group.

The term "halo" means one or more hydrogen atoms of the group are replaced by halogen groups.

The terms "alkylthio" or "alkylthio group" mean a monovalent radical of the formula AlkS—, where Alk is alkyl. Exemplary groups include methylthio, ethylthio, n-propylthio, isopropylthio, n-butylthio, and the like.

The terms "sulfonyl" or "sulfonyl group" mean a divalent radical of the formula —$SO_2$—.

The terms "carbocycle" or "carbocyclic group" mean a stable aliphatic 3- to 15-membered monocyclic or polycyclic monovalent or divalent radical consisting solely of carbon and hydrogen atoms which may comprise one or more fused or bridged ring(s), preferably a 5- to 7-membered monocyclic or 7- to 10-membered bicyclic ring. Unless otherwise specified, the carbocycle may be attached at any carbon atom which results in a stable structure and, if substituted, may be substituted at any suitable carbon atom which results in a stable structure. The term comprises cycloalkyl (including spiro cycloalkyl), cycloalkylene, cycloalkenyl, cycloalkenylene, cycloalkynyl, and cycloalkynylene, and the like.

The terms "cycloalkyl" or "cycloalkyl group" mean a stable aliphatic saturated 3- to 15-membered monocyclic or polycyclic monovalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornanyl, adamantyl, tetrahydronaphthyl(tetralin), 1-decalinyl, bicyclo[2.2.2]octanyl, 1-methylcyclopropyl, 2-methylcyclopentyl, 2-methylcyclooctyl, and the like.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The terms "heterocycle", "heterocycle group", "heterocyclyl", or "heterocyclyl group" mean a stable non-aromatic 5- to 14-membered monocyclic or polycyclic, monovalent or divalent, ring which may comprise one or more fused or bridged ring(s), preferably a 5- to 7-membered monocyclic or 7- to 10-membered bicyclic ring, having from one to three heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Exemplary and preferred heterocycles include pyrrolinyl, pyrrolidinyl, pyrazolinyl, pyrazolidinyl, piperidinyl, morpholinyl, thiomorpholinyl, piperazinyl, tetrahydropyranyl, tetrahydrothiopyranyl, tetrahydrofuranyl, hexahydropyrimidinyl, hexahydropyridazinyl, and the like.

The term "compounds of the invention" and equivalent expressions are meant to embrace compounds of Formula (I) as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The term "chiral auxiliary" means a chiral compound that can be temporarily covalently attached to a substrate of interest to induce diastereoselectivity in subsequent chemical transformations, after which the chiral auxiliary is often cleaved off the substrate. Chiral auxiliaries are well known in the art, see, for example, Chapter 1 in Jacqueline Seyden-Penne, *Chiral Auxiliaries and Ligands in Asymmetric Synthesis*, Wiley: New York (1995), which is herewith incorporated by reference, but are not limited thereto. Chiral auxiliaries amenable to the present invention include those that can be covalently coupled to carboxylic acid (e.g., alcohols and amines). Representative chiral auxiliaries include, without limitation, menthol, 8-phenylmenthol, trans-2-phenyl-1-cyclohexanol, norephedrine-derived chiral alcohols, and cis-amonoindinol derived chiral alcohols.

The term "Seyden-Penne chiral auxiliary" is a chiral auxiliary disclosed in Jacqueline Seyden-Penne, *Chiral Auxiliaries and Ligands in Asymmetric Synthesis*, Wiley: New York (1995).

The term "condensing agent" means a reagent that can couple a free carboxylic acid with an alcohol or amine to form esters or amides respectively. Such condensing agents are well known in the art, see, for example, Richard C. Larock, *Comprehensive Organic Transformations*, Wiley-VCH, New York (1999), which is hereby incorporated by reference, but are not limited thereto.

The term "Larock condensing agent" is a condensing agent disclosed in Richard C. Larock, *Comprehensive Organic Transformations*, Wiley-VCH, New York (1999).

The term "hydrolyzing agent" means a reagent that could convert a carboxylic acid derivative (e.g. amides or esters) to a free carboxylic acid. Examples of such hydrolyzing agents are described in Richard C. Larock, *Comprehensive Organic Transformations*, Wiley-VCH, New York (1999), but are not limited thereto.

The term "Larock hydrolyzing agent" is a hydrolyzing agent disclosed in Richard C. Larock, *Comprehensive Organic Transformations*, Wiley-VCH, New York (1999).

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 $R^5$, then such group is optionally substituted with up to two $R^5$ groups and $R^5$ at each occurrence is selected independently from the defined list of possible $R^5$. Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

EXPERIMENTAL EXAMPLES

The invention provides processes for making compounds of Formula (I). In all schemes, unless specified otherwise, $R^1$ to $R^5$ in the formulas below can have the meanings of $R^1$ to $R^5$ in the Trifluoromethyl-Substituted Alcohol Patent Applications. Intermediates used in the preparation of compounds of the invention are either commercially available or readily prepared by methods known to those skilled in the art. For example, 2-(2-chloro-1,1-dimethylethyl)-4-fluoro-1-methoxybenzene was synthesized by heating a mixture of 4-fluoroanisole, methallyl chloride, and sulfuric acid at 50° C.

The epoxide of Formula (II) is a key intermediate in the synthesis of certain racemic compounds of Formula (I), as described in U.S. patent application Pub. No. 2004/0162321 (corresponding to PCT International Publication No. WO 2004/063163), which is hereby incorporated by reference. Treatment of the epoxide of Formula (II) with the nucleophile $R^5H$, in the presence of base opens the epoxide to provide racemic (I) as shown below in Scheme I Scheme I

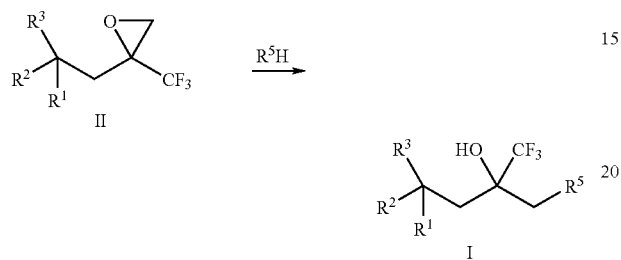

The stereoselective synthesis of a single enantiomer of epoxide (II) is described below. Preparation of the desired enantiomer of Formula (I) can then be achieved by reaction of enantiomerically pure (II) with the appropriate nitrogen, oxygen, sulfur, or carbon nucleophile ($R^5H$).

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Experimental Examples section. Typically, reaction progress may be monitored by high performance liquid chromatography (HPLC) or thin layer chromatography (TLC), if desired, and intermediates and products may be purified by chromatography on silica gel and/or by recrystallization.

SYNETHETIC EXAMPLES

The following is a representative example that illustrates the process of the invention. HPLC used to characterize products and intermediates were done on a $C_{18}$ Super-ODS column (Supelco, part no. 818197, 4.6 mm×10 cm) eluting with a gradient of 5% acetonitrile/95% water/0.05% TFA to 95% acetonitrile/5% water/0.05% TFA over 15 minutes and then held at 95% acetonitrile/5% water/0.05% TFA for 5 minutes. References to concentration or evaporation of solutions refer to concentration on a rotary evaporator.

Example 1

Synthesis of (R)-2-[2-(5-fluoro-2-methoxyphenyl)-2-methylpropyl]-2trifluoromethyloxiran

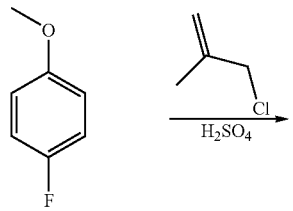

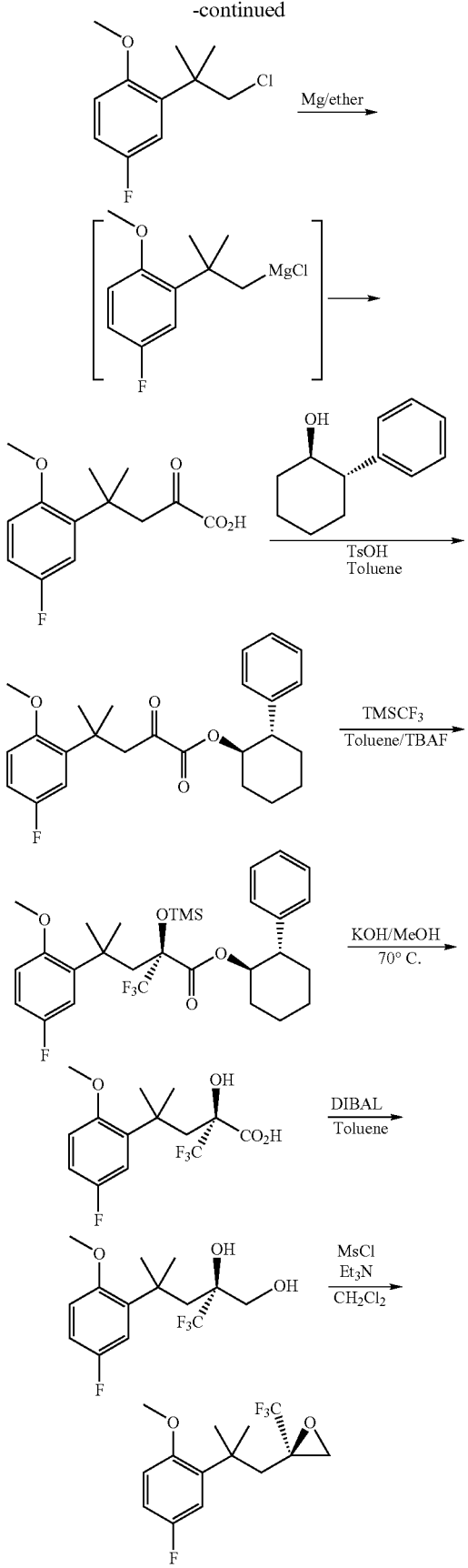

Magnesium turnings (46 g, 1.89 mol) were placed in a 5000 mL three-neck flask equipped with a mechanical stirrer and an additional funnel. The flask was heated to 120° C. under vacuum and then flushed with nitrogen while cooling to ambient temperature. This procedure was repeated three times, then the flask was cooled to ambient temperature and kept under a constant nitrogen blanket. Anhydrous diethyl ether (1000 mL) was added and the mixture was stirred at approximately 260 rpm. Dibromoethane (86.25 g, 0.46 mol) was added to the mixture through the addition funnel over about 1 hour while the temperature was kept between 22° C. and 27° C. The addition of dibromoethane to the flask was exothermic and water cooling was applied to maintain this temperature range.

2-(2-Chloro-1,1-dimethylethyl)-4-fluoro-1-methoxybenzene (100 g, 0.46 mol) and dibromoethane (86.25 g, 0.46 mol) were dissolved in anhydrous diethyl ether (1000 mL) and the resulting solution was loaded into the addition funnel. The solution was added to the reaction mixture over 3.5 hours while the temperature was kept between 22° C. and 25° C. The reaction was stirred at room temperature for 16 hours. HPLC showed no starting material remained and a ratio of desired Grignard reagent to Wurtz coupling by-product of 94 area % to 6 area %.

The reaction mixture was cooled to −70° C. and diethyl oxalate (99.6 g, 0.69 mol) in 100 mL of diethyl ether was added over about 15 minutes while maintaining the internal temperature below −65° C. The reaction was allowed to stir at or below −65° C. for 6 hours. 2N HCl (250 mL) and 300 mL of water were added to the slurry while stirring at 300 rpm. The clear two-phase solution was allowed to warm up to ambient temperature and stirred for 0.5 hour. After phase separation, the organic layer was washed once with water (500 mL) and concentrated. The resulting crude product mixture was dissolved in 250 mL THF at −10° C. 2 N NaOH (600 mL) was added at a rate that maintained the temperature below 10° C. The reaction was then warmed to room temperature for 15 minutes. The resulting slurry was filtered and the cake was washed with three 50 mL portions of 1 N NaOH. The aqueous solution was extracted with two 300 mL portions of $CH_2Cl_2$ and then the aqueous layer was acidified to pH 1 to 2 using 6 N HCl. Then the acid was extracted with $CH_2Cl_2$ (1×600 mL; 1×200 mL). Toluene (200 mL) was added to the combined organic layers and the resulting solution was dried over magnesium sulfate ($MgSO_4$). Filtration and concentration gave 94 g of 4-(5-fluoro-2-methoxyphenyl)-4-methyl-2-oxopentanoic acid as an oil (yield: 80% from starting chloride).

The above carboxylic acid (66.52 g, 271.3 mmol) and (1R,2S)-2-phenylcyclohexanol were placed in a 1000 mL flask, followed by the TsOH—$H_2O$ and toluene. The mixture was refluxed (with stirring) for 3 to 8 hours with removal of water from the reaction mixture by collection in a Dean-Stark trap, until HPLC showed that the chiral auxiliary was reacted completely.

The reaction mixture was cooled to room temperature and then was washed with three 125 mL portions of aqueous $NaHCO_3$ solution (5%), and one 125 mL portion of brine. The organic layer was separated and evaporated to give 99.8 g (96%) 4-(5-fluoro-2-methoxyphenyl)-4-methyl-2-oxopentanoic acid (1R,2S)-2-phenylcyclohexyl ester as an oil.

The above ester (10 g, 24.2 mmol) was placed in a dry 250 mL three-neck flask equipped with a mechanical stirrer and under a constant nitrogen flush. Anhydrous toluene (100 mL) was added and the mixture was stirred at approximately 200 rpm to dissolve the oil, forming a slightly yellow clear solution. $TMSCF_3$ (5.2 g, 36.4 mmol) was added and the solution was cooled to −26° C. TBAF (1.2 mL, 1.2 mmol of a 1 M solution in THF) was added slowly while the internal temperature was kept below −15° C. The resulting solution was stirred at −20° C. for 5 minutes before it was allowed to warm up to room temperature. After 30 minutes, HPLC analysis indicated that there was no ester left and that the desired 4-(5-fluoro-2-methoxyphenyl)-4-methyl-(2S)-2-trifluoromethyl-2-(tris-silanylmethoxy)pentanoic acid (1R,2S)-2-phenylcyclohexyl ester was formed in a 5:1 diastereomeric excess over the unwanted diastereomer. Water (20 mL) was added to the flask and the mixture is then stirred for 15 minutes. The layers were separated and the organic layer was washed with 20 mL of brine. Solvent was removed under vacuum and the oil was chased with 40 mL heptane to yield 14.2 g crude product as an orange oil. Under vigorous agitation, 30 mL MeOH was added. After about 5 minutes, white crystals appeared. After the mixture was stirred for 15 minutes, the solid was filtered and washed with 5 mL MeOH twice and dried. The desired (2S,1'R,2'S)-isomer (6.75 g, 50%) was obtained as a white crystalline compound. The diastereomeric excess and purity were both >99% (HPLC peak area).

The above ester (9.0 g, 16.2 mmol) was added into a KOH/MeOH solution made from 3.6 g KOH and 45 mL MeOH. The mixture was heated at reflux (70° C.) for 15 hours and the HPLC indicated complete reaction. 50 mL of $CH_2Cl_2$ and 50 mL of $H_2O$ were added. The layers were separated and the aqueous layer was extracted with 50 mL of $CH_2Cl_2$ again. The combined organic layers were set aside for later recovery of the chiral auxiliary.

The aqueous layer was checked by HPLC for complete removal of residual auxiliary. The aqueous layer was then acidified to pH 2 using 5 N HCl and the product was extracted with two 75 mL portions of $CH_2Cl_2$. The combined organic layers were dried over magnesium sulfate and concentrated to give 5.1 g of (S)-4-(5-fluoro-2-methoxyphenyl)-2-hydroxy-4-methyl-2-trifluoromethylpentanoic acid (96% yield).

The above carboxylic acid (5.1 g dissolved in 10 mL THF) was added slowly to a solution of 62.8 mL of a 1.5 M solution of diisobutylaluminum hydride (DIBAL) in toluene at −30° C. The reaction mixture was warmed up to room temperature and kept at this temperature for 3 hours. The reaction mixture was cooled to 0° C. and quenched with 200 mL of aqueous 1 M NaK tartrate solution. The reaction mixture was stirred at room temperature for 15 minutes and then filtered through diatomaceous earth. The layers were separated and the organic layer was dried over magnesium sulfate and concentrated to dryness to give (R)-4-(5-fluoro-2-methoxyphenyl)-4-methyl-2-trifluoromethylpentane-1,2-diol (4.5 g, 92% yield).

A solution of the above diol (4.4 g) in $CH_2Cl_2$ (50 mL) was cooled to −30° C. and treated with triethylamine (9.9 mL). Methanesulfonyl chloride (1.34 mL) was added slowly over about 20 minutes so that the reaction temperature was kept below −20° C. The resulting suspension was gradually warmed to room temperature and stirred for 14 hours. The mixture was diluted with methyl tert-butyl ether (50 mL), washed with three 30 mL portions of 5% NaHCO₃ aqueous solution, and concentrated to give the title compound as a colorless oil (4.1 g, 100%).

Two additional examples for the key asymmetric trifluoromethyl addition step are provided below to facilitate the understanding of the present invention.

Example 2

Asymmetric Trifluoromethyl Addition to Alkyl Substituted Ketoester

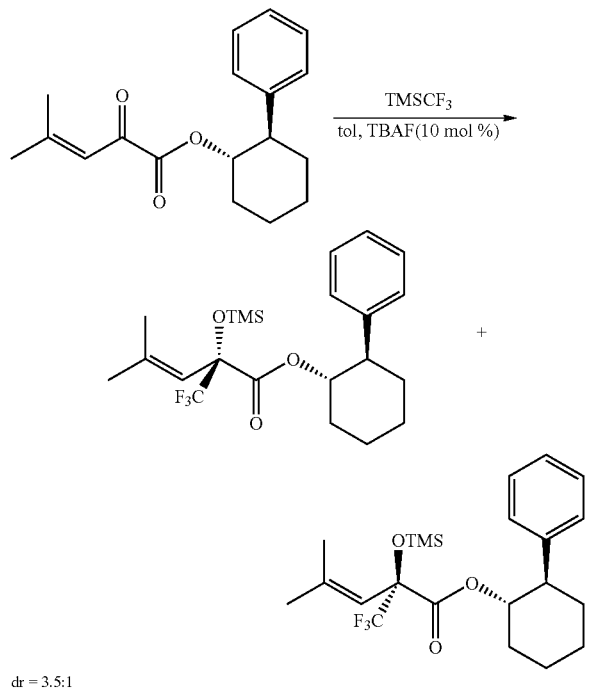

dr = 3.5:1

Using the trans-2-phenyl-1-cyclohexanol as the auxiliary, we have demonstrated that an alkyl substituted ketoester also underwent auxiliary-controlled asymmetric trifluoromethyl addition.

Example 3

Asymmetric Trifluoromethyl Addition Using Different Auxiliaries

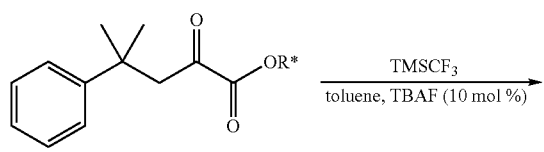

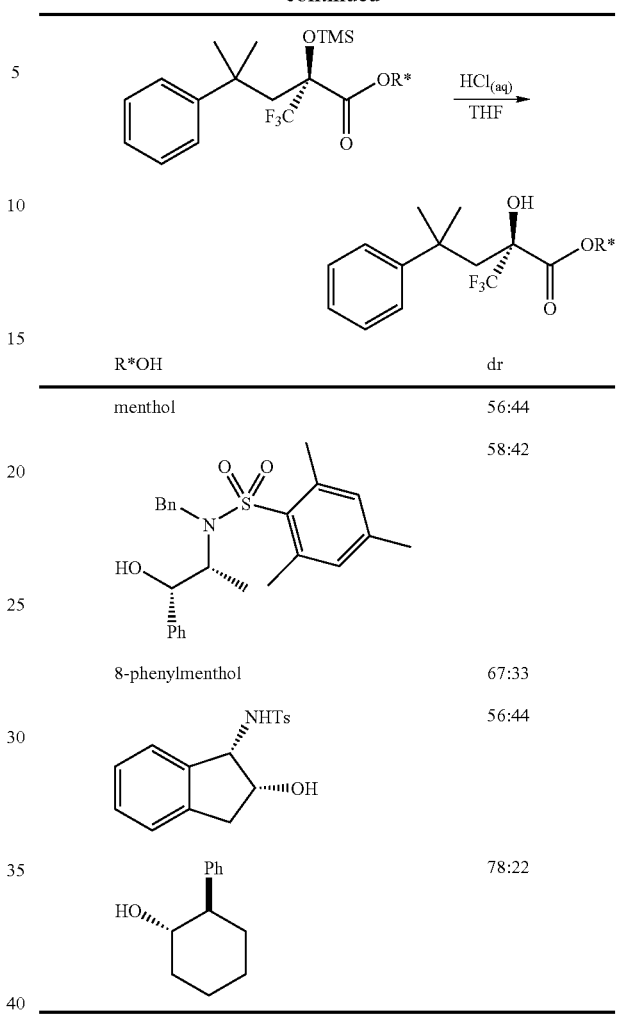

| R*OH | dr |
|---|---|
| menthol | 56:44 |
| | 58:42 |
| 8-phenylmenthol | 67:33 |
| | 56:44 |
| | 78:22 |

For the phenyl substituted case, a number of chiral auxiliaries have been examined experimentally. In all cases, asymmetric induction was observed.

What is claimed is:
1. A process for stereoselective synthesis of a compound of Formula X

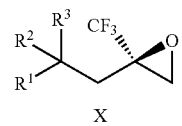

X wherein:
R¹ is an aryl or heteroaryl group, each optionally independently substituted with one to three substituent groups, wherein each substituent group of R¹ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, $C_1$-$C_5$ alkanoyloxy, $C_1$-$C_5$ alkanoyl, aroyl, trifluoromethyl, trifluoromethoxy, or $C_1$-$C_5$ alkylthio,
wherein each substituent group of R¹ is optionally independently substituted with one to three substituent groups selected from methyl, methoxy, fluoro, chloro, or hydroxy; and $R^2$ and $R^3$ are each independently hydrogen or $C_1$-$C_5$ alkyl, or $R^2$ and $R^3$ together with the carbon atom they are commonly attached to form a $C_3$-$C_8$ spiro cycloalkyl ring, the process comprising:

(a) reacting the starting material of formula A where X is Cl, Br, or I, with magnesium metal in a suitable solvent to prepare a Grignard intermediate of formula B

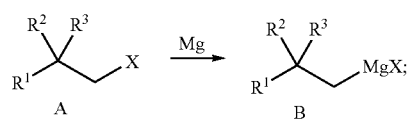

(b) reacting the Grignard intermediate of formula B with a disubstituted oxalate of formula C, where $R^{10}$ is an alkyl or aryl group, in a suitable solvent to obtain a compound of formula D

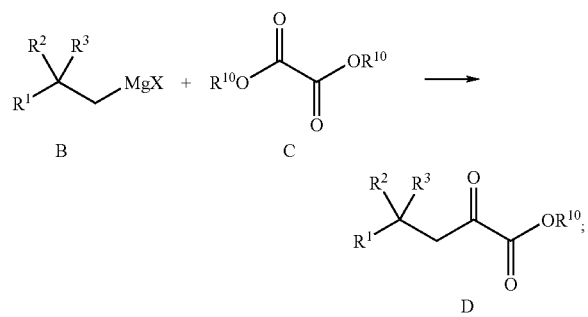

(c) hydrolyzing the compound of formula D in a suitable solvent to obtain the carboxylic acid of formula E

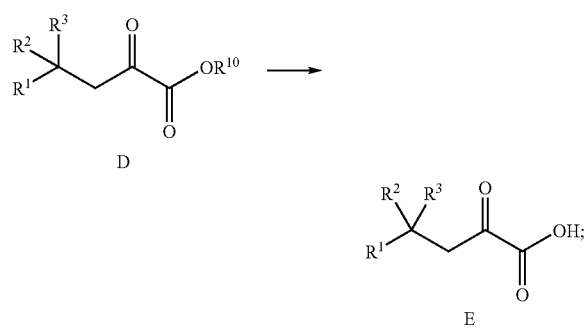

(d) coupling the carboxylic acid of formula E with R*ZH, where R*ZH is a chiral auxiliary and R* is a chiral residue and Z is O or NH, in a suitable solvent to obtain a compound of formula F

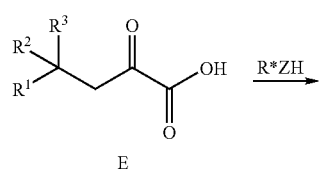

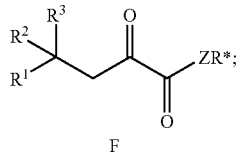

(e) reacting the compound of formula F with trifluoromethide ion source $YCF_3$ in a suitable solvent to make the compound of formula G

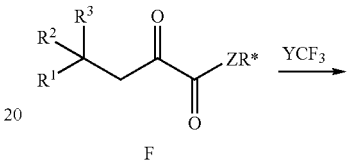

(f) hydrolyzing the compound of formula G to remove the chiral auxiliary group R*ZH and obtain the compound of formula H

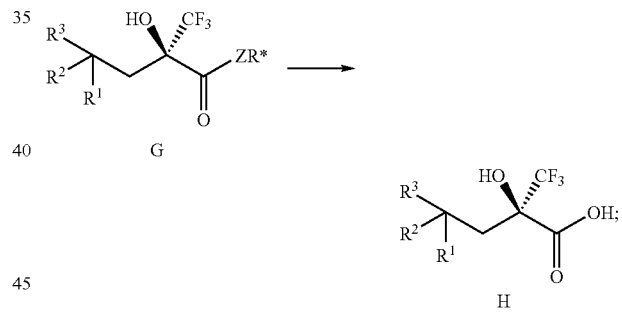

(g) reducing the compound of formula H to obtain the compound of formula I

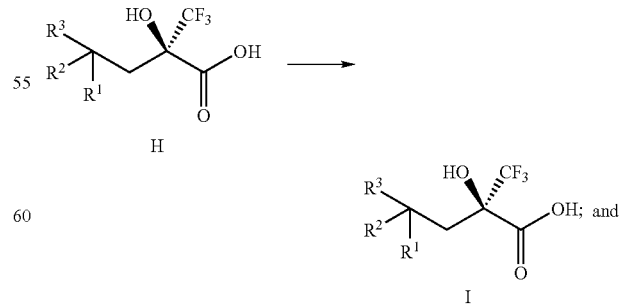

(h) cyclizing the compound of formula I to obtain the epoxide compound of formula X

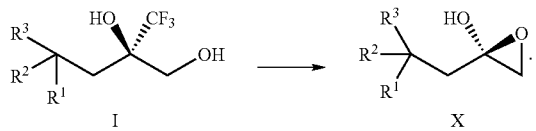

2. The process according to claim 1, wherein the suitable solvent of step (a) is selected from dimethyl ether, diethyl ether, dipropyl ether, diisopropyl ether, dibutyl ether, tetrahydrofuran (THF), ethylene glycol dimethyl ether (DME), tert-butyl methyl ether (MTBE), or a mixture thereof.

3. The process according to claim 1, wherein the suitable solvent of step (a) is selected from diethyl ether or tetrahydrofuran.

4. The process according to claim 1, wherein the suitable solvent of step (b) is selected from diethyl ether, dipropyl ether, diisopropyl ether, dibutyl ether, tetrahydrofuran (THF), ethylene glycol dimethyl ether (DME), tert-butyl methyl ether (MTBE), or a mixture thereof.

5. The process according to claim 1, wherein the suitable solvent of step (b) is selected from diethyl ether or tetrahydrofuran.

6. The process according to claim 1, wherein the hydrolysis of step (c) is accomplished with an alkaline metal hydroxide, phase transfer hydrolysis, or acid hydrolysis in a suitable solvent selected from tetrahydrofuran (THF), methanol, ethanol, water, DME, MTBE, IPA, dimethyl ether, dipropyl ether, diisopropyl ether, or mixture of these solvents.

7. The process according to claim 1, wherein the suitable solvent of step (c) is selected from dimethyl ether, diethyl ether, tetrahydrofuran (THF), or a mixture thereof.

8. The process according to claim 1, wherein the suitable solvent of step (d) is selected from: toluene, benzene, xylene, hexane, pentane, heptane, acetonitrile, methylene chloride, ethyl acetate, or a mixture thereof.

9. The process according to claim 1, wherein the reaction of step (d) is accomplished using a condensing agent.

10. The process according to claim 9, wherein the condensing agent is 1,3-dicyclohexylcarbodiimide (DCC) or 1-(dimethylaminopropyl)-3-ethylcarbodiimide hydrochloride (EDC).

11. The process according to claim 9, wherein the condensing agent is a Larock condensing agent.

12. The process according to claim 1, wherein R*ZH is a Seyden-Penne chiral auxiliary.

13. The process according to claim 1, wherein in R*ZH, Z is O.

14. The process according to claim 1, wherein in R*ZH, Z is NH.

15. The process according to claim 1, wherein in R*ZH is menthol, 8-phenylmenthol, trans-2-phenyl-1-cyclohexanol, a norephedrine-derived chiral alcohol, or a cis-aminoindinol derived chiral alcohol.

16. The process according to claim 1, wherein the suitable solvent of step (e) is selected from: diethyl ether, methylene chloride, toluene, benzene, acetonitrile, N,N-dimethylformamide (DMF), tetrahydrofuran (THF), tert-butyl methyl ether (MTBE), or a mixture thereof.

17. The process according to claim 1, wherein the chiral auxiliary group R*ZH is recovered during or after step (f).

18. The process according to claim 1, wherein the trifluoromethide ion source YCF$_3$ is selected from TMS-CF$_3$ and TES-CF$_3$.

19. The process according to claim 1, wherein an initiator is used in step (e).

20. The process according to claim 19, wherein the initiator is tetrabutylammonium fluoride (TBAF), tetrabutylammonium triphenyldifluorosilicate (TBAT), a trialkylamine, a trialkylphosphine, cesium fluoride, potassium fluoride, DMAP, or pyridine.

21. The process according to claim 1, wherein the hydrolysis of step (f) is accomplished using a hydrolyzing agent which is KOH/ROH, where R is a lower alkyl group.

22. The process according to claim 1, wherein the reduction of step (g) is accomplished using a reducing agent selected from diisobutylaluminum hydride (DIBAL), 65 wt. % solution of sodium bis(2-methoxyethoxy)aluminum hydride in toluene (Red-Al®), borane-iodine complex, borane-sulfuric acid complex, lithium aluminum hydride (LAH), or 9-borabicyclo [3.3.1] nonane (9-BBN).

23. The process according to claim 1, wherein the suitable solvent of step (g) is selected from diethyl ether, toluene, tetrahydrofuran (THF), tert-butyl methyl ether (MTBE), hexanes, or a mixture thereof.

24. The process according to claim 1, wherein the cyclizing of step (h) is accomplished using a sulfonyl halide.

25. The process according to claim 1, wherein the sulfonyl halide is selected from mesitylenesulfonyl chloride (MsCl) or p-toluenesulfonyl chloride (TsCl).

26. The process according to claim 1, wherein the cyclizing of step (h) is accomplished with a suitable organic or inorganic base.

27. The process according to claim 26, wherein the suitable base is selected from triethylamine (TEA), diisopropylethylamine (DIEA), pyridine, lutidine, or potassium carbonate.

* * * * *